(12) United States Patent
Chang

(10) Patent No.: US 7,618,509 B2
(45) Date of Patent: Nov. 17, 2009

(54) WRINKLED BAND WITHOUT AIR EXPANSION TUBE AND ITS MANUFACTURING METHOD

(76) Inventor: Ickchun Chang, #8-501 6th Yeonse River Vill, #184-1, Gwangjang-Dong, Gwangjin-Gu, Seoul 143-210 (KR)

( * ) Notice: Subject to any disclaimer, the term of this patent is extended or adjusted under 35 U.S.C. 154(b) by 623 days.

(21) Appl. No.: 10/595,903

(22) PCT Filed: Mar. 13, 2004

(86) PCT No.: PCT/KR2004/000537

§ 371 (c)(1),
(2), (4) Date: May 18, 2006

(87) PCT Pub. No.: WO2005/048889

PCT Pub. Date: Jun. 2, 2005

(65) Prior Publication Data

US 2007/0125485 A1    Jun. 7, 2007

(30) Foreign Application Priority Data

Nov. 18, 2003  (KR)  ............... 10-2003-0081866
Nov. 18, 2003  (KR)  ............... 10-2003-0081867
Dec. 30, 2003  (KR)  ............... 10-2003-0100651

(51) Int. Cl.
*A61F 5/00*  (2006.01)

(52) U.S. Cl. ............... 156/161; 156/163; 156/164; 156/229; 156/290; 156/308.2; 602/13; 128/118.1; 128/96.1

(58) Field of Classification Search .......... 156/161, 156/160, 163, 164, 229, 308.2; 602/13; 128/118.1, 128/96.1, DIG. 20
See application file for complete search history.

(56) References Cited

U.S. PATENT DOCUMENTS

| 3,559,213 | A | * | 2/1971  | Goodman ............... 2/237 |
| 4,135,503 | A | * | 1/1979  | Romano ............... 602/13 |
| 4,682,587 | A | * | 7/1987  | Curlee ............... 602/13 |
| 4,682,588 | A | * | 7/1987  | Curlee ............... 602/13 |
| 4,703,750 | A |   | 11/1987 | Sebastian et al. |
| 5,450,858 | A | * | 9/1995  | Zablotsky et al. ...... 128/876 |
| 5,728,055 | A | * | 3/1998  | Sebastian ............ 602/19 |
| 5,980,560 | A |   | 11/1999 | Chang |

FOREIGN PATENT DOCUMENTS

| JP | 08-071094       |   | 3/1996  |
| JP | 08-191850       |   | 7/1996  |
| JP | 2000-288004 A   | * | 10/2000 |
| KR | 100142202       |   | 3/1998  |
| KR | 1020000044058   |   | 7/2000  |
| KR | 1020000066548   |   | 11/2000 |
| KR | 1020000073327   |   | 12/2000 |

* cited by examiner

*Primary Examiner*—Jeff H Aftergut
(74) *Attorney, Agent, or Firm*—IPLA P.A.; James E. Bame

(57) ABSTRACT

The present invention relates to a belt-type wrinkled band used for healing a hernia of intervertebral disk or protection the intervertebral disk. In particular, the expansion and contraction by air-injection can be achieved, without using a rubber tube for the contraction and expansion.

6 Claims, 11 Drawing Sheets

WRINKLED BAND WITHOUT AIR EXPANSION TUBE AND ITS MANUFACTURING METHOD

TECHNICAL FIELD

The present invention relates to a wrinkled band for healing a hernia of intervertebral disk or protecting the intervertebral disk, in which the wrinkled band tightly worn around the waist is expanded vertically by air-injection to stretch in-between of the lumbar. In particular, the invention relates to such a wrinkled band, in which the expansion and contraction by air-injection can be achieved, without using a rubber tube for the contraction and expansion.

BACKGROUND ART

The conventional wrinkled band has a band 100 having a constant vertical width. An air-expansion tube 100, which is expanded to have substantially the same width as the vertical width of the band, is fixed inside the band 100 by means of a sewing means. Thereafter, the air of the air-expansion tube 110 is removed such that the band 100 is transformed into a wrinkled band.

This conventional technique is disclosed in Korean Patent No. 142202. Each upright air-expansion tube 110 is vertically connected to each connector 120 in a single direction. The connector 120 is not to be expanded. Thereafter, only the air-expansion tube 110 is housed in a separate pocket 130 with the air-expansion tube 110 being expanded. Then, the pocket 130 is connected, using a sewing means, to a band 100 having substantially the same width as the expanded air-expansion tube 110. The air of the air-expansion tube 110 is removed to thereby provide a wrinkled band. However, disadvantageously this technique needs many connectors, and the connection of the air-expansion tube 110 to the connector 120 is manually carried out using a pressuring band 140. In addition, when these many connector 120 is expanded by a strong air pressure, the connection portion between the connector 120 and the air-expansion tube 110 is prone to be burst, or air-leakage is occurred due to non-uniform pressuring.

Therefore, in order to solve these problems, recently, Korean Patent No. 298328 has proposed a technique, in which a single air-expansion tube 210 is formed in zigzags and placed inside a band 200 having a constant width. After that, the air-expansion tube 210 is seal-adhered to the band 200 using a sewing means, while the air-expansion tube 210 is expanded by air-injection.

However, as one disadvantage of the above approach, when the single air-expansion tube 210 is formed in zigzags, a curved portion 220 is created in the upper and lower portion thereof. In the case where this curved portion is formed closely to each other, the upper and lower curved portion 220 is folded, and thus the air-injection is impeded due to the folding of the curved portion. In order to avoid the folding of the curved portion 220, the spacing 230 between the curved portions is made larger, a strong force cannot be achieved, thereby failing to obtain a desired effect.

In addition, since this separate air-expansion tube 210 is accommodated inside the band 200, when wearing the band in the waist, the user feels a sense of foreign matters with the air-expansion tube 210 being expanded. Since the width of the wrinkled band 200 is larger in the center portion thereof, as compared with both end portions thereof, the both end portions having a relatively narrower width is stretched when the center portion thereof is extended. Therefore, the center portion of the band is likely to be flipped backwards, thereby deteriorating a comfort sense of wearing.

DISCLOSURE OF INVENTION

Therefore, the present invention does not use a separate air-expansion tube, and an adhesion line is formed by an adhesion of an overlapped sheet to thereby form an expansion space inside thereof. The upper and lower portion of the expansion is adhered simultaneously while the adhesion line is formed with an elastic means being stretched, thereby providing a wrinkled band. When adhered, the adhesion is performed while the elastic means is stretched, so that the bonding force of the elastic means is prevented from being deteriorated, due to the resilience created by stretching.

In addition, the wrinkled band can be closely and tightly fitted into the waist of the user, and can minimize the pressurizing of a certain specific portion of the waist, even while wearing the band for a long time.

BRIEF DESCRIPTION OF DRAWINGS

Further objects and advantages of the invention can be more fully understood from the following detailed description taken in conjunction with the accompanying drawings, in which.

BEST MODE FOR CARRYING OUT THE INVENTION

Figure 1:
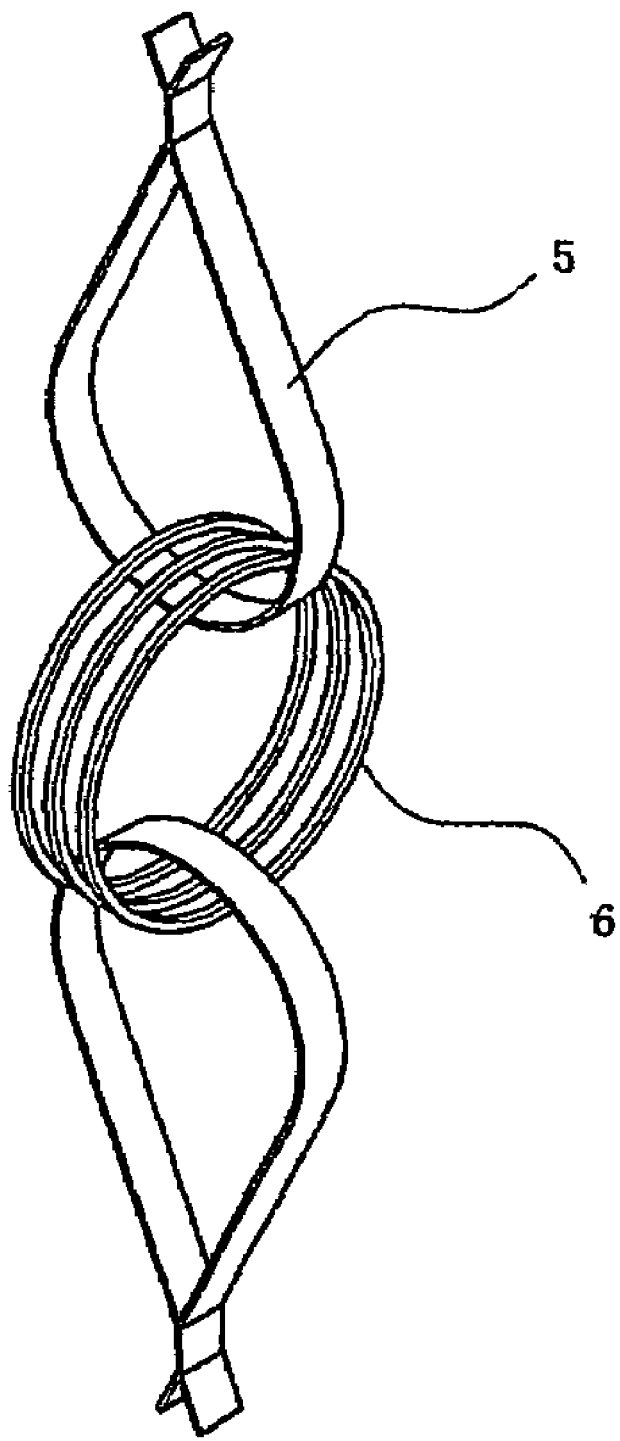
FIG. 1 is a perspective view showing a connection of an elastic band with a connection adhesion band according to one embodiment of the invention.

The preferred embodiments of the present invention will be hereafter described in detail with reference to the accompanying drawings. In the drawings, like elements are denoted by like reference numerals.

Figure 7A:
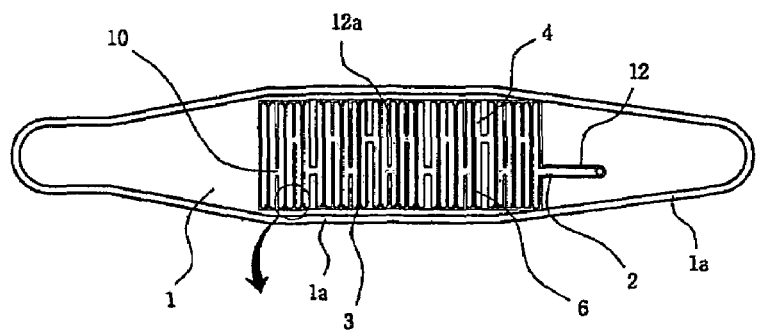
FIG. 7A is a plan view of a wrinkled band when it is expanded.
Figure 7B:
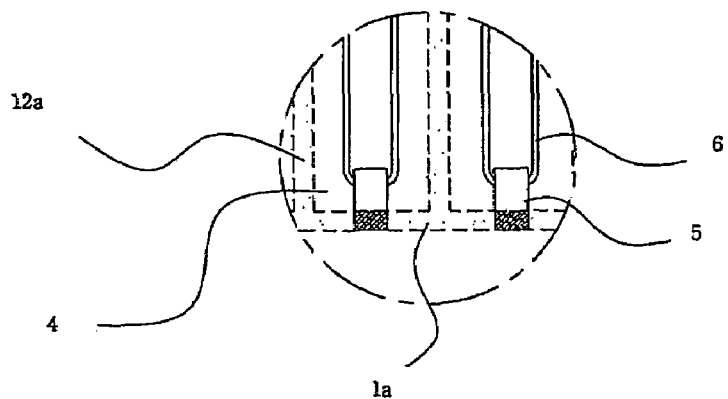
FIG. 7B is a plan view of a connection adhesion band when it is adhered.
Figure 8:
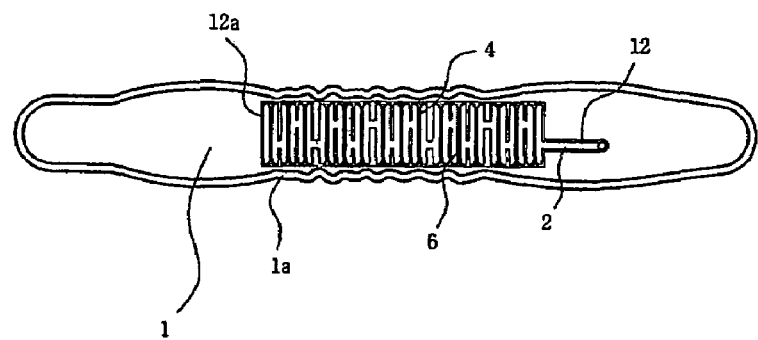
FIG. 8 is a plan view of a wrinkled band when it is pleated.
Figure 9:
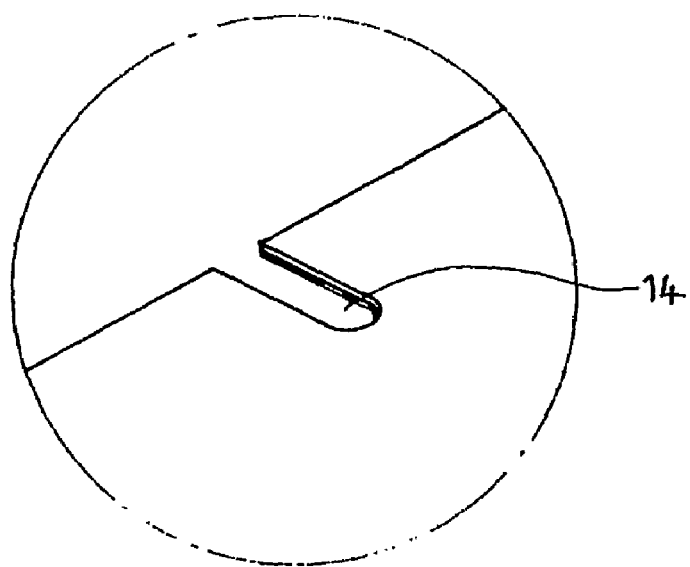
FIG. 9 shows the formed structure of a cut portion.
Figure 10:
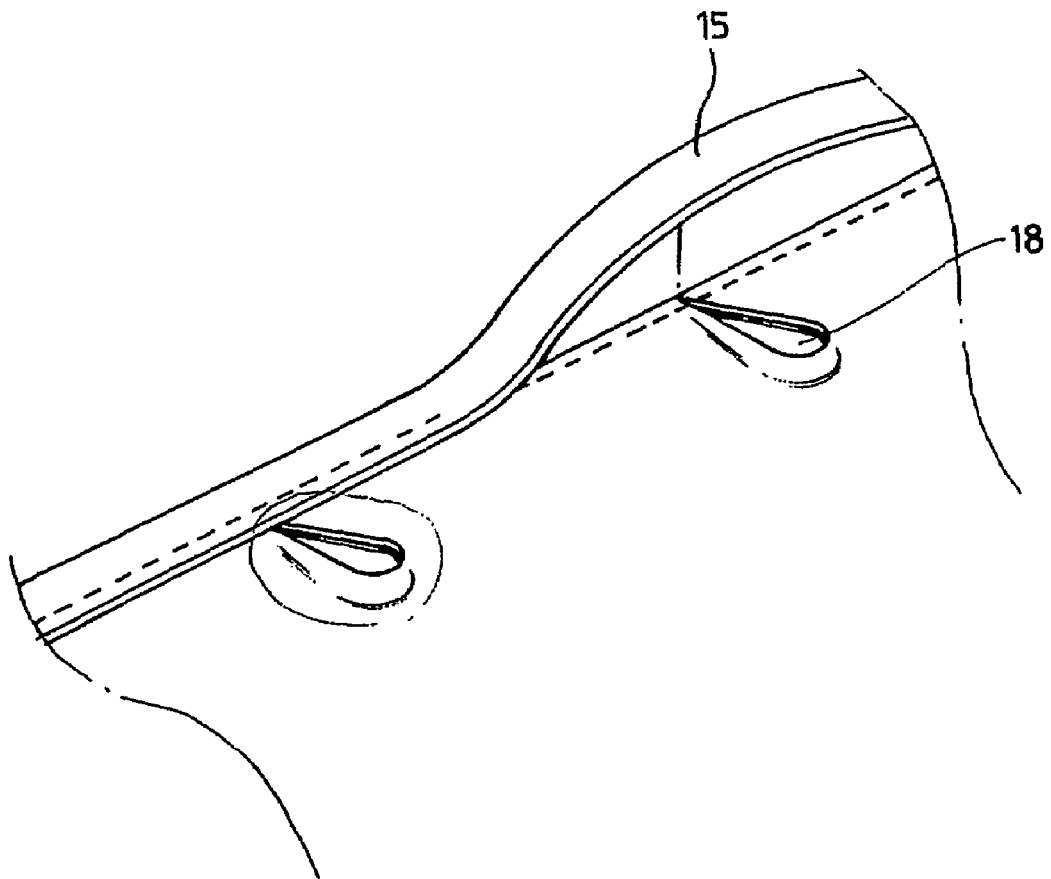
FIG. 10 is a perspective view where a margin is embodied.
Figure 11:
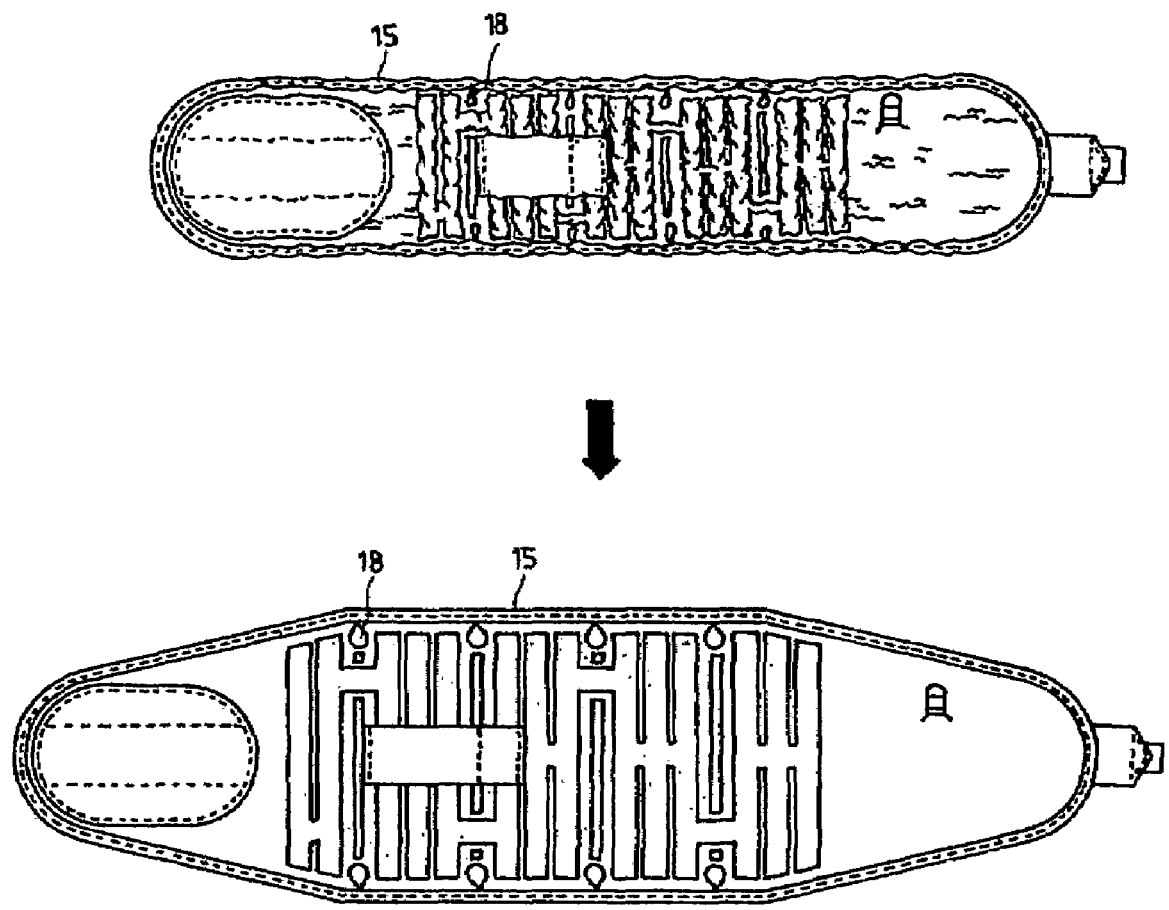
FIG. 11 illustrates an operational state of the margin.
Figure 12:
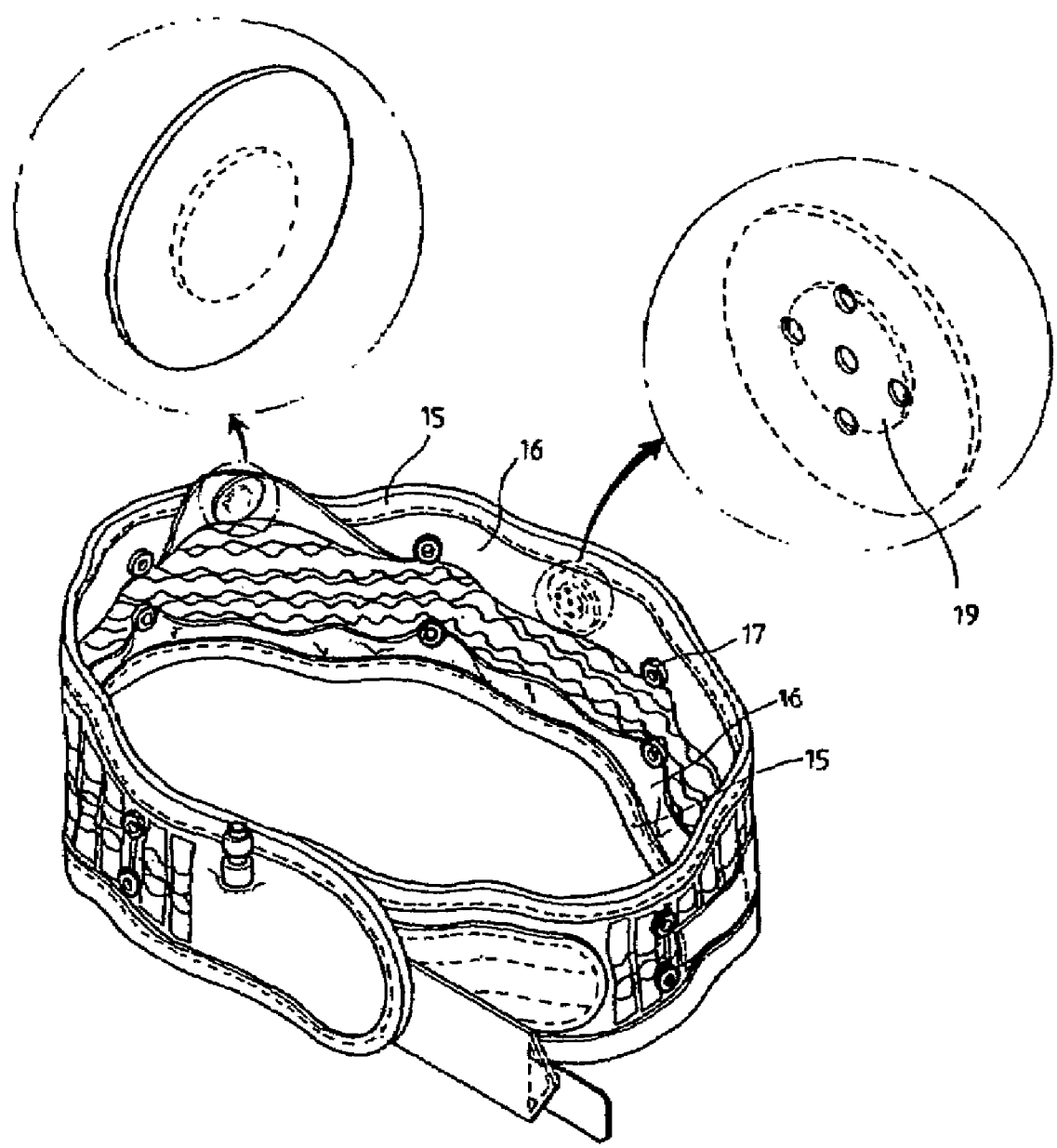
FIG. 12 is a perspective view showing a protective pad according to one embodiment of the invention.
Figure 13:
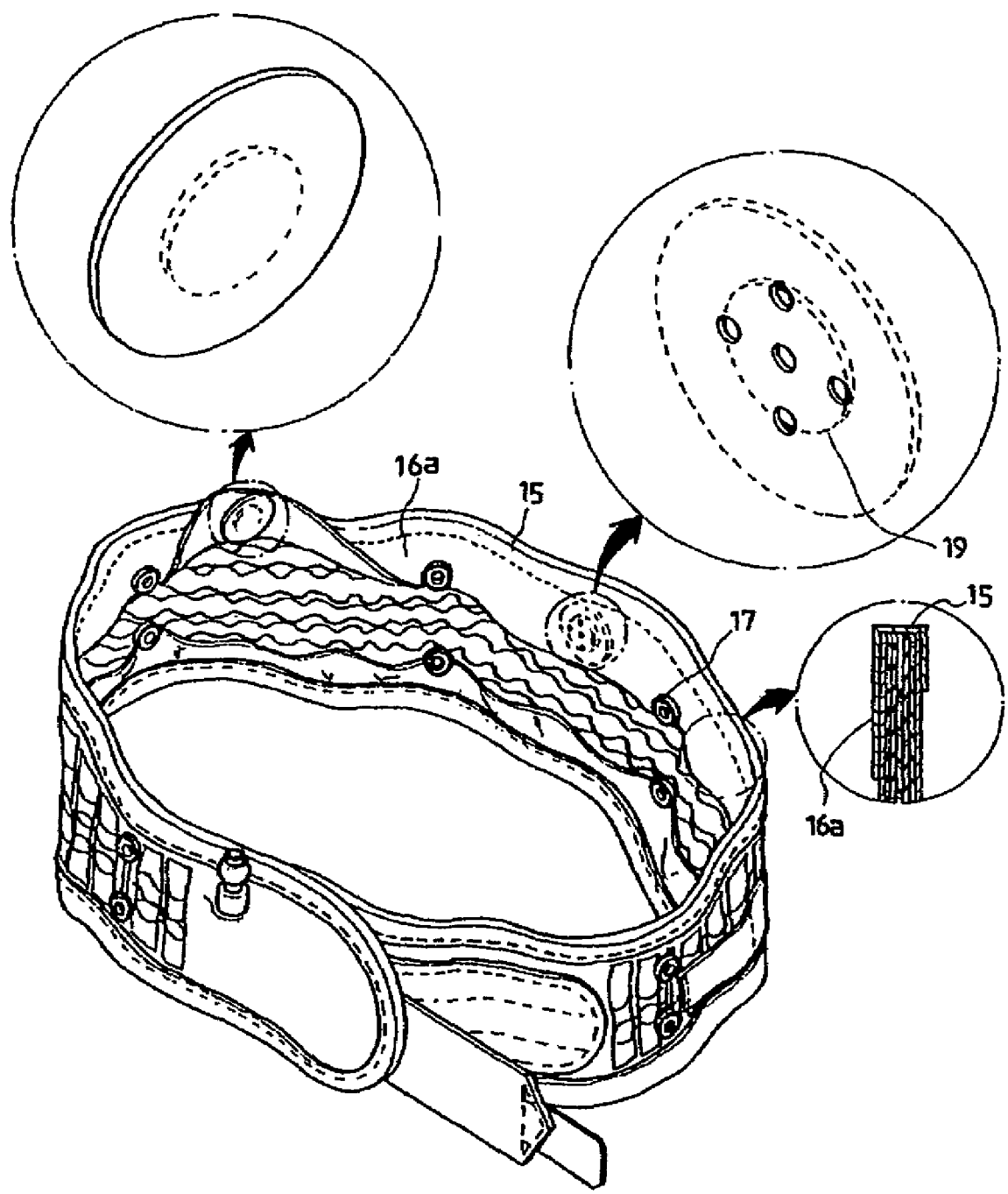
FIG. 13 is a perspective view showing a protective pad according to another embodiment of the invention.
Figure 14:
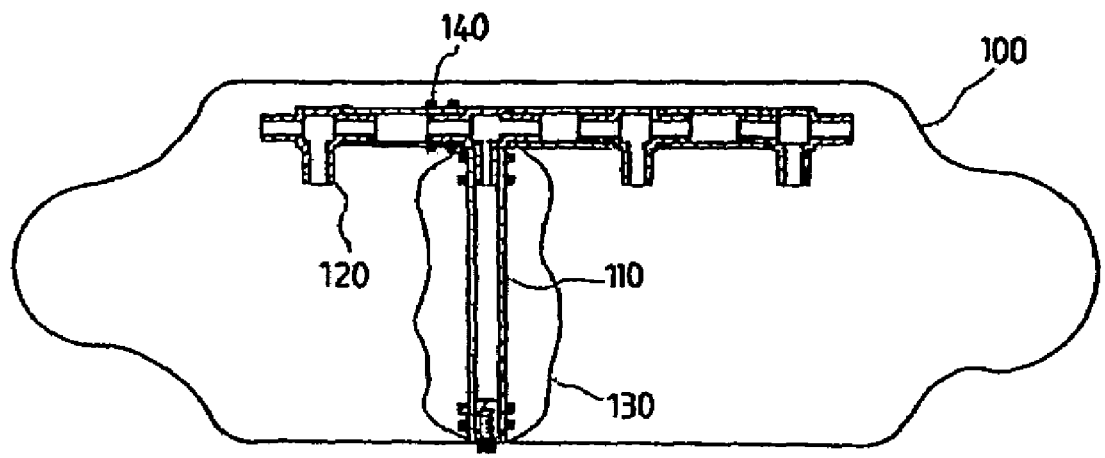
FIG. 14 is a schematic view showing a conventional wrinkled band.
Figure 15:
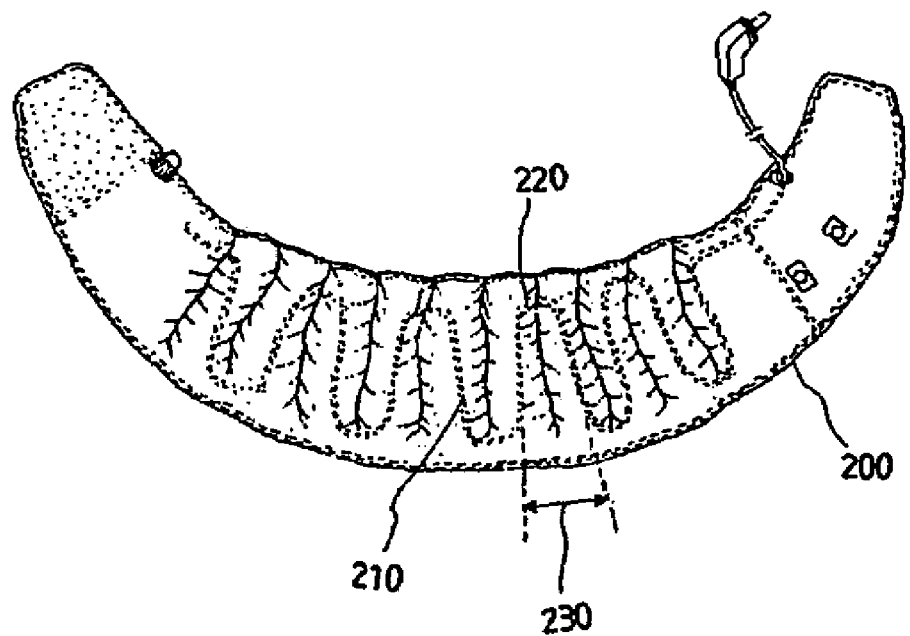
FIG. 15 is a schematic view showing another conventional wrinkled band.

As illustrated in FIG. 7, an adhesion line 12 is formed with a certain regularity inwards the inner face while adhering the outer peripheral rim 1a of an adhesion sheet 1 to be overlapped, and thus an air passage 2 is obtained. In addition, an inner space 4 is secured at regular intervals by another adhesion line 12a. A connection adhesion band 5 is adhered upper and lower of the inner space 4 by the outer peripheral rim 1a. An elastic band 6 is connected to the connection adhesion band 5.

Figure 3:
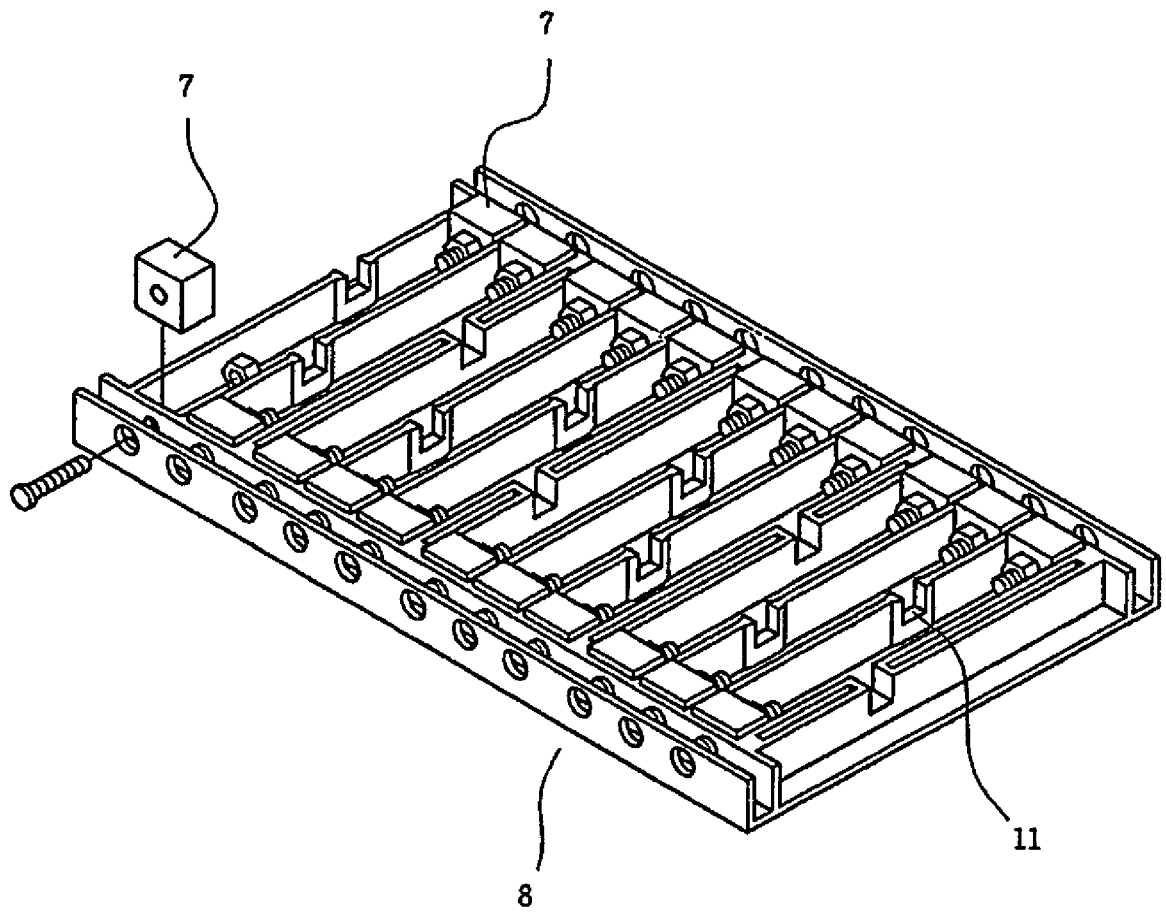
FIG. 3 shows the structure of the operating die of a high frequency operated die.
Figure 4:
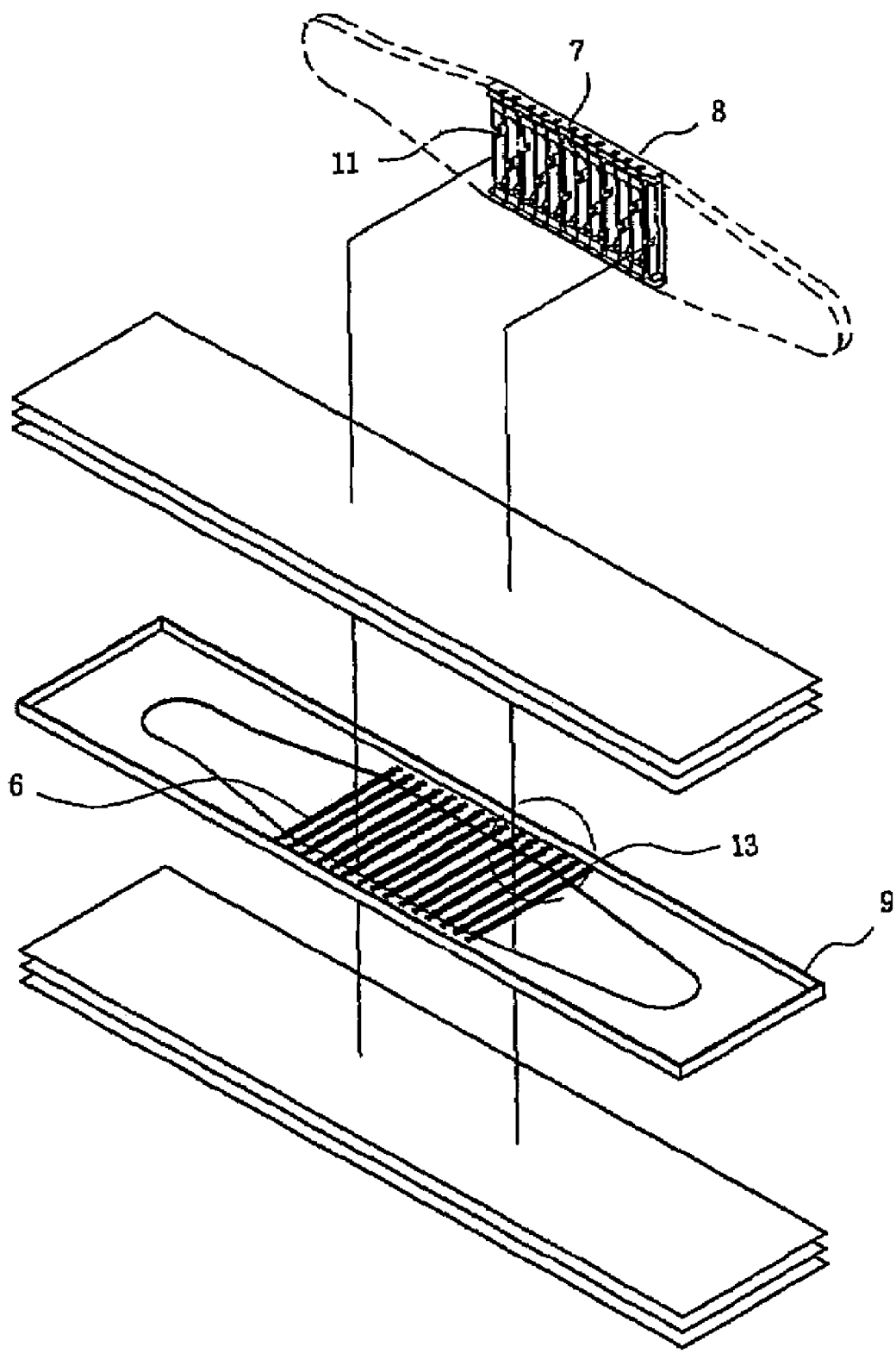
FIG. 4 shows a fabricating construction of the invention.
Figure 5:
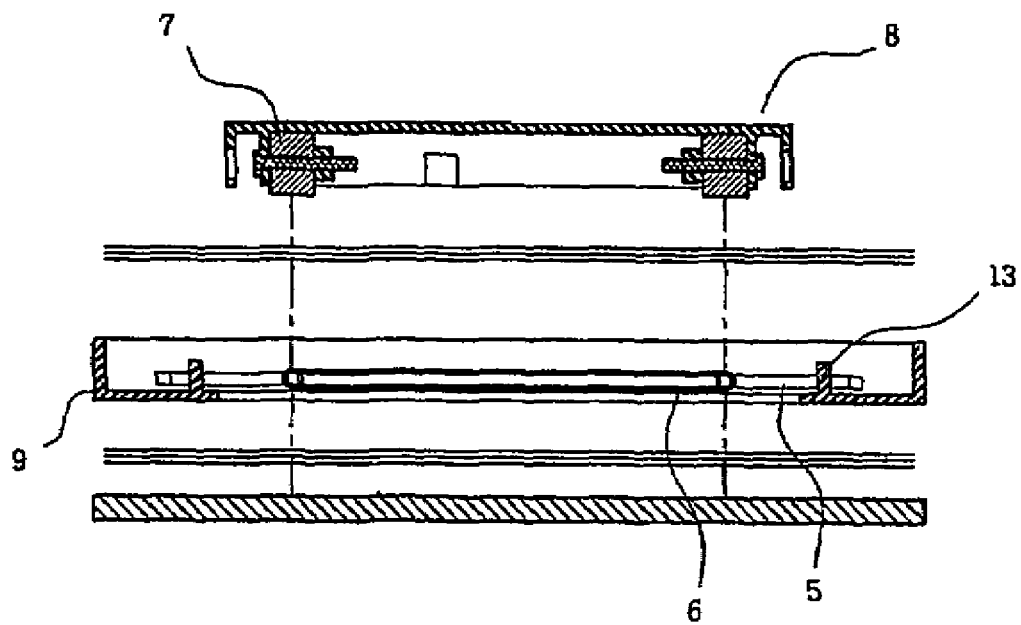
FIG. 5 is a cross-section showing the operation of the high frequency operated die before its pressurizing means is pressed.
Figure 6:
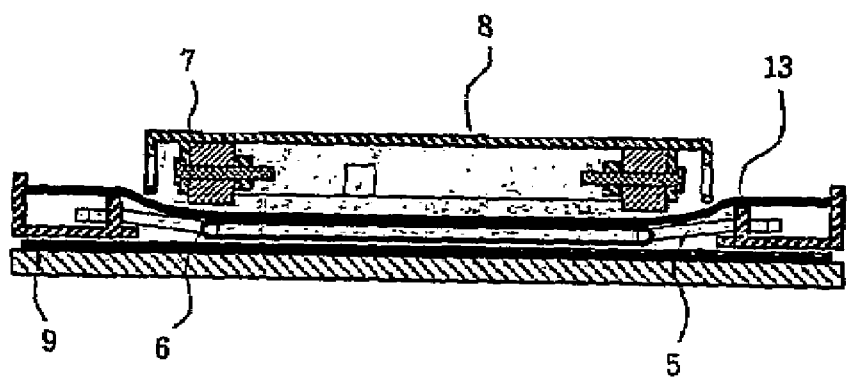
FIG. 6 is a cross-section showing the operation of the high frequency operated die after its pressurizing means is pressed.

At this time, the adhesion line 12a partitioning the inner space 4 is not adhered with a constant width so that a vent hole 10 is formed. As illustrated in FIG. 3, the vent hole 10 may be formed by a cut groove 11 of a high-frequency operating die 8.

In addition, this vent hole 10 is formed as so to be offset from a neighboring vent hole, and thus when air is injected into the inner space 4, almost perfect and uniform expansion is carried out almost at the same time.

Figure 2A:
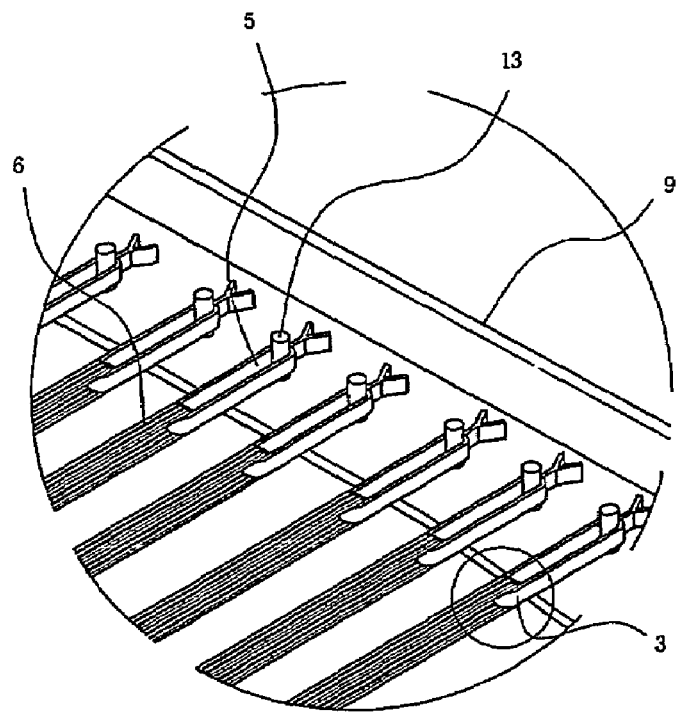
FIG. 2A is a perspective view showing the connection adhesion band mounted on a mounting die.
Figure 2B:
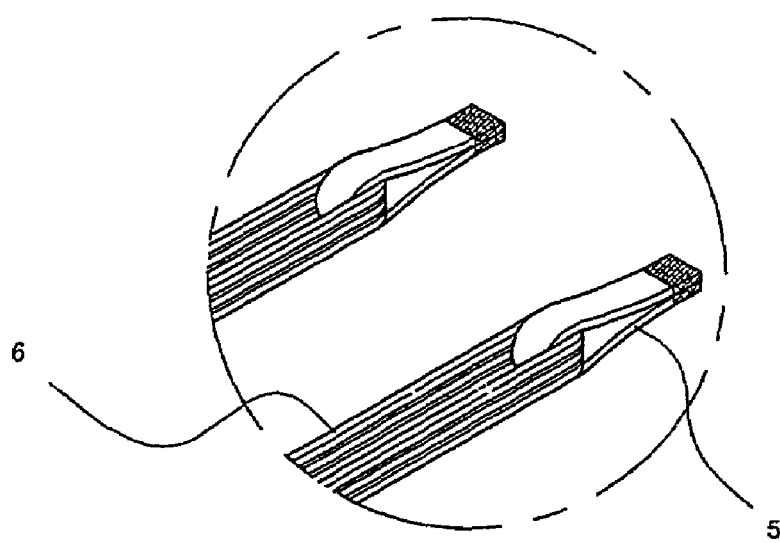
FIG. 2B illustrates the adhered state of the connection adhesion band.

Furthermore, in the case where the connection adhesion band 5 is adhered to the outer peripheral line 1a, as shown in FIGS. 1 and 2, a boundary portion 3, where the elastic band 6 and the connection adhesion band 5 are connected, is made to be primarily pressed using a pressurizing means 7 formed in the high-frequency operating die 8.

Thereafter, if the connection adhesion band 5 is adhered separately or simultaneously along the outer peripheral line 1a, the pressurizing means 7 mounted on the high-frequency operating die 8 preliminarily pressurizes and presses the boundary portion 3, where the stretched state of the elastic band 6 is maintained. Therefore, the stretching force of the elastic band is not transferred to the connection adhesion band 5, which is to be adhered to the outer peripheral line 1a. In the case where the connection adhesion band 5 is melted to be softened and thus adhered with the outer peripheral line 1a, also the adhesion is easily performed because of no load. After this adhesion is completed, the cooling is finished by a natural or forced cooling. Therefore, the connection adhesion band 5, which has been softened by melting when adhered, is restored to its original state, so that no damage occurs.

At this time, the high-frequency operating die 8 is operated upward and downward by a mechanical operation (not shown). The mounting die 9, on which the connection adhesion band 5 connected with the elastic band 6 is mounted, is engaged with the high-frequency operating die 8, and at this time the overlapped sheet 1 mounted on the mounting die 9 is adhered. Thus, the outer peripheral line 1a and the adhesion line 12a are adhered, and simultaneously the connection adhesion band 5 is adhered with the outer peripheral line 1a.

After that, as illustrated in FIG. 2, when the connection adhesion band 5 mounted on the high-frequency mounting die 9 is removed from the connecting portion 13, the overlapped sheet 1 is pleated by means of the elastic band 6.

Therefore, since no damage occurs in the connection adhesion band 5 even by the high-frequency adhesive bonding, no damage occurs in the wrinkled band by the expansion and contraction of the elastic band, which is caused by the repeated expansion and contraction of the inner space 4.

In addition, the wrinkled band is formed in such a manner that its center portion has a width wider, relative to both ends thereof. Therefore, after a cut portion 14 is formed in the upper edge, the upper end of the cut portion 14 is wrapped with a separate rim sleeve 15 and seal-adhered and fixed thereto, such that the upper edge is prevented from being flipped backwards when expanded.

At this time, after the cut portion 14 is cut in the form of U-shape, the both upper portions of the cut portion 14 are made to contact so as to make a margin 18, and then wrapped and seal-adhered with the rim sleeve 15. This seal-adhesion prevents both side ends of the wrinkled band to flipping backwards Owing to the margin 18 of the cut portion 14. This is, when the wrinkled band is stretched in a vertical direction, the center portion of the wrinkled band is stretched more relatively to the both end portions since it has a wider width relatively to the both end portions thereof. Therefore, the elastic band is also more stretched, and the both side ends thereof is less stretched relatively so that it tends to be flipped backward duet to a pulling force generated by the differential stretching. At this time, the backward flipping is prevented due to the margin 18 of the cut portion 14 in the wrinkled band.

In addition, before the rim sleeve 15 of the band is seal-adhered, a protective pad wing 16 is provided in the inner side of the band. The protective pad wing 16 is seal-adhered by a separate rim sleeve 15, which is formed in such a way that the upper and lower end edge of the band is wrapped around. Or, the protective pad wing 16a can be simply fabricated by extending longer one side of the above rim sleeve 15.

The protective pad wings 16 and 16a is fixed to the inner side face of the band by means of a fixing member 17 such a rivet, thereby avoiding the fluttering of it.

Furthermore, the protective pad wing 19 may be provided with a blood circulation aid 19 for promoting blood circulation. The blood circulation aid includes a magnet, or a precious stone, germanium, or the like having a far infrared radiation effect.

INDUSTRIAL APPLICABILITY

Therefore, since the wrinkled band of the invention does not use a separate air-expansion, the spacing between the inner spaces can be formed densely to the extent not to have any gap in-between. In the case where the adhesion is carried out to the center of the inner space 4 formed by the adhesion line 12a of the overlapped adhesion sheet 1, in the state where the elastic band 6 is stretched, the boundary portion 3 for a resilient force to be exerted is pressed and fixed by the pressurizing means 7 of the high-frequency operating die 8, and thereafter adhered by melting and cooling it. Therefore, no defect occurs in the resultant product.

In addition, the wrinkled band is formed in such a manner that its central portion has a convex shape, relatively to both side ends thereof. Therefore, when the band is stretched vertically by air-injection, due to the margin 18 created by fixing the rim sleeve 15 to the cut portion 14, the upper and lower edge portions are prevented from being flipped backwards. In the case where a user wears the wrinkled band for a long time, he or she does not feel a sense of foreign matters by means of the protective pad wing 16.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A method of manufacturing a wrinkled band, wherein the outer peripheral rim of an overlapped adhesion sheet is adhered and simultaneously an adhesion line having an air passage is formed with certain regularity in the inner side face thereof, another adhesion line forms a respective vent hole and secures an inner space in-between, and above and below the secured inner space a connection adhesion band 5 with an elastic band 6 connected thereto is adhered by an outer peripheral line, with the elastic band being stretched.

2. The method according to claim 1, wherein, in the case where the connection adhesion band 5 is adhered with the outer peripheral line 1a, a boundary portion 3, where the elastic band 6 and the connection adhesion band 5 are connected, is primarily pressurized and fixed by a pressurizing means 7 of a high-frequency die, and thereafter the connection adhesion band is adhered with an adhesion surface and then cooling is performed by a cooling means.

3. The method according to claim 2, wherein the pressurizing means 7 is made of an elastic body and directly mounted on the high-frequency operating die 8.

4. The method according to claim 1, wherein the vent hole is formed in such a way to be offset from a corresponding vent hole.

5. The method according to claim 2, wherein the connection adhesion band is hung on a connecting portion of a mounting die of the high-frequency die such that the stretched state of the elastic band is maintained.

6. The method according to claim 2, wherein the connection band is constructed in a band-type in such a manner that a strip-like thing is fined into an elastic band of band-type and then its leading end is adhered.

\* \* \* \* \*